(12) United States Patent
Skraber

(10) Patent No.: US 10,973,673 B1
(45) Date of Patent: Apr. 13, 2021

(54) ORTHOPEDIC FIXATION ASSEMBLY AND ORTHOPEDIC FIXATION SYSTEM

(71) Applicant: Geoffrey Skraber, Auburn, CA (US)

(72) Inventor: Geoffrey Skraber, Auburn, CA (US)

( * ) Notice: Subject to any disclaimer, the term of this patent is extended or adjusted under 35 U.S.C. 154(b) by 460 days.

(21) Appl. No.: 15/683,064

(22) Filed: Aug. 22, 2017

Related U.S. Application Data

(60) Provisional application No. 62/477,310, filed on Mar. 27, 2017.

(51) Int. Cl.
*A61F 5/042* (2006.01)
*A61H 1/00* (2006.01)

(52) U.S. Cl.
CPC .............. *A61F 5/042* (2013.01); *A61H 1/006* (2013.01)

(58) Field of Classification Search
CPC .. A61F 5/04; A61F 5/042; A61F 5/048; A61F 5/05; A61H 1/006; A61H 1/008; A61H 1/02; A61H 1/0222; A61H 1/0218; A61H 1/0237; A61H 1/0248; A61H 1/0251; A61G 13/0009; A61G 13/0081; A61G 13/1245; A61G 13/0063; A61G 15/005
USPC ............................ 602/23, 33, 34, 35, 36, 38
See application file for complete search history.

(56) References Cited

U.S. PATENT DOCUMENTS

| | | | | |
|---|---|---|---|---|
| 1,898,781 A | * | 2/1933 | Leiter | A61F 5/04 |
| | | | | 602/33 |
| 4,643,177 A | * | 2/1987 | Sheppard | A61F 13/041 |
| | | | | 602/40 |
| 5,669,908 A | * | 9/1997 | Gracilla | A61F 5/04 |
| | | | | 602/23 |

* cited by examiner

*Primary Examiner* — Rachael E Bredefeld
*Assistant Examiner* — William T Kao
(74) *Attorney, Agent, or Firm* — Ice Miller LLP

(57) ABSTRACT

An orthopedic fixation assembly, an orthopedic fixation system, and a traction bow assembly are provided. The orthopedic fixation assembly includes a first arm configured for positioning at a first side of a traction location, a second arm configured for positioning at a second side of the traction location, and a joint connecting the first arm to the second arm.

13 Claims, 6 Drawing Sheets

US 10,973,673 B1

ORTHOPEDIC FIXATION ASSEMBLY AND ORTHOPEDIC FIXATION SYSTEM

RELATED APPLICATION DATA

This application claims the priority benefit of U.S. Provisional Application Ser. No. 62/477,310, filed Mar. 27, 2017, which is hereby incorporated in its entirety herein by reference.

BACKGROUND OF THE DISCLOSED EMBODIMENTS

Particular circumstances, including an increase in vehicles in many countries, have increased the frequency of skeletal fractures, such as femur and pelvic fractures to name non-limiting examples, in pedestrians and animals, such as when struck by vehicles. Upon fracturing a bone, such as a femur, a person is typically immobilized for a period of time during which the leg is placed in traction.

Traction involves positioning a pin, wire, screw, or other object through the fractured bone. A traction bow, a Kirschner wire tractor, or similar device typically fixes the pin, wire, screw, or other object from each side of the fractured bone or another nearby bone. The traction bow or other device is attached to an orthopedic fixation system or structure to apply tension to and/or fix the traction bow or other device and/or bone to create and maintain the necessary tractive force to keep the fractured ends of the bone in a desired relationship, often against contractive forces of the large muscles, such as one or more structures or systems described in *Zimmer Traction Handbook: A Complete Reference Guide to the Basics of Traction*, published in 2006 by Zimmer Orthopaedic Surgical Products, Inc. and hereby incorporated by reference in its entirety herein.

For some fractures, the traction device may be positioned at a limb extremity. Due to the geometry of conventional traction devices, a portion of the limb or body part, such as a knee in the case of a femur fracture, may contact, press against, or otherwise interfere with the traction device. Such interference may result in discomfort, pressure sores, or even lacerations to the limb or body part. Further, a conventional traction bow assembly includes several moveable parts between a rotating adjustment part and expandable arms. The collection of interconnected parts results in imprecise control and a relatively loose and insecure assembly.

Accordingly, there exists a need for an orthopedic fixation assembly, an orthopedic fixation system, and a traction bow assembly that provide a desired tractive force without discomfort or injury to the patient. Further, there exists a need for an orthopedic fixation assembly, an orthopedic fixation system, and a traction bow assembly that improve control and handling of the conventional traction device.

SUMMARY OF THE DISCLOSED EMBODIMENTS

In an embodiment of the present disclosure, an orthopedic fixation assembly is provided. The assembly includes a first arm configured for positioning at a first side of a traction location, a second arm configured for positioning at a second side of the traction location, and a joint connecting the first arm to the second arm for adjustment of the first arm and the second arm along an adjustment plane, the first arm having a first arm end portion being distal from the joint and angled from the adjustment plane by a downward angle, and the second arm having a second arm end portion being distal from the joint and angled from the adjustment plane by the downward angle.

In an embodiment of the present disclosure, an orthopedic fixation system is provided. The system includes a stationary traction member configured to apply a pulling force to a traction location, and a traction bow assembly configured for positioning at the traction location and having an attachment portion attached to the stationary traction member, a first arm having a first arm end portion, and a second arm having a second arm end portion, an end plane defined between the first arm end portion, the second arm end portion, and the attachment portion, the first arm having a first arm central portion and the second arm having a second arm central portion such that the first arm central portion and the second arm central portion are spaced from the end plane.

In an embodiment of the present disclosure, a traction bow assembly is provided. The assembly includes an attachment portion configured for attachment to a stationary traction member, a first arm, and a second arm. The first arm includes a first arm end portion distal from the attachment portion and a first arm central portion. The second arm includes a second arm end portion distal from the attachment portion a second arm central portion. The first arm end portion, the second arm end portion, and the attachment portion form an end plane. The first arm central portion and second arm central portion are spaced from the end plane.

BRIEF DESCRIPTION OF DRAWINGS

The embodiments described herein and other features, advantages, and disclosures contained herein, and the manner of attaining them, will become apparent and the present disclosure will be better understood by reference to the following description of various exemplary embodiments of the present disclosure taken in conjunction with the accompanying drawing, wherein.

DETAILED DESCRIPTION OF THE DISCLOSED EMBODIMENTS

Figure 1:
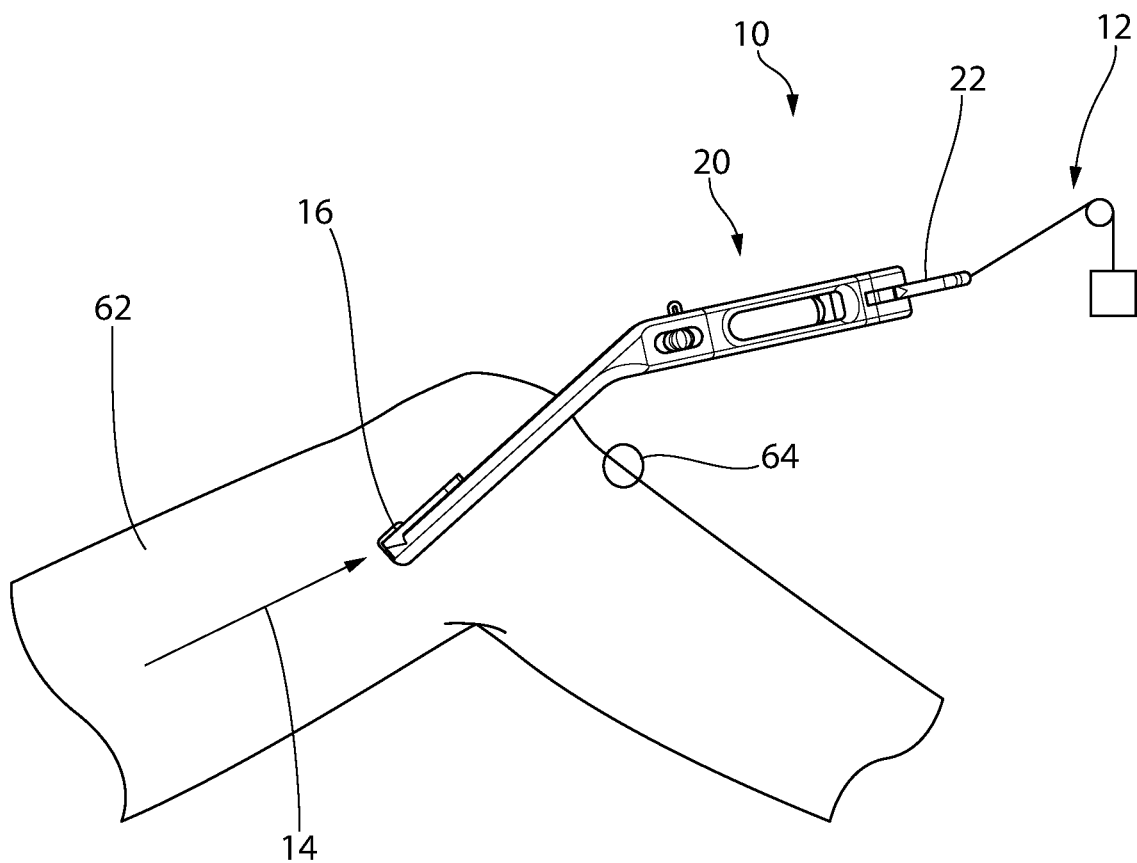
FIG. 1 is a right side elevation view of an orthopedic fixation system according to an embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

FIG. 1 schematically illustrates an orthopedic fixation system 10 in accordance with an embodiment of the present disclosure. The system 10 includes a stationary traction member 12 configured to apply a pulling force 14 to a traction location 16. The traction location 16 may be a location on a patient's limb 62, such as a leg or arm, but may also include any body part or location known by a person having ordinary skill in the art. The system 10 may include any structures or techniques known to a person having ordinary skill in the art, including without limitation those structures and techniques disclosed in the incorporated publication *Zimmer Traction Handbook: A Complete Reference Guide to the Basics of Traction*, published in 2006 by Zimmer Orthopaedic Surgical Products, Inc.

The system 10 includes an orthopedic fixation assembly or traction bow assembly 20. The terms "orthopedic fixation assembly" and "traction bow assembly" are intended to include the same structure, features, operation, and benefits, and will be commonly referred to as "fixation assembly 20" in the present disclosure for any fixation or traction bow assembly embodiment. The system 10 may include the fixation assembly 20 and/or any other component related to traction systems and/or methods recognized by one of ordinary skill in the art. As illustrated in FIG. 1, the fixation assembly 20 is configured for positioning at the traction location 16. The fixation assembly 20 includes an attachment portion 22 attached to the stationary traction member 12. The attachment portion 22 may be attached to the stationary traction member 12 by rope, strapping, cable, or similarly functioning structure.

Figure 2:
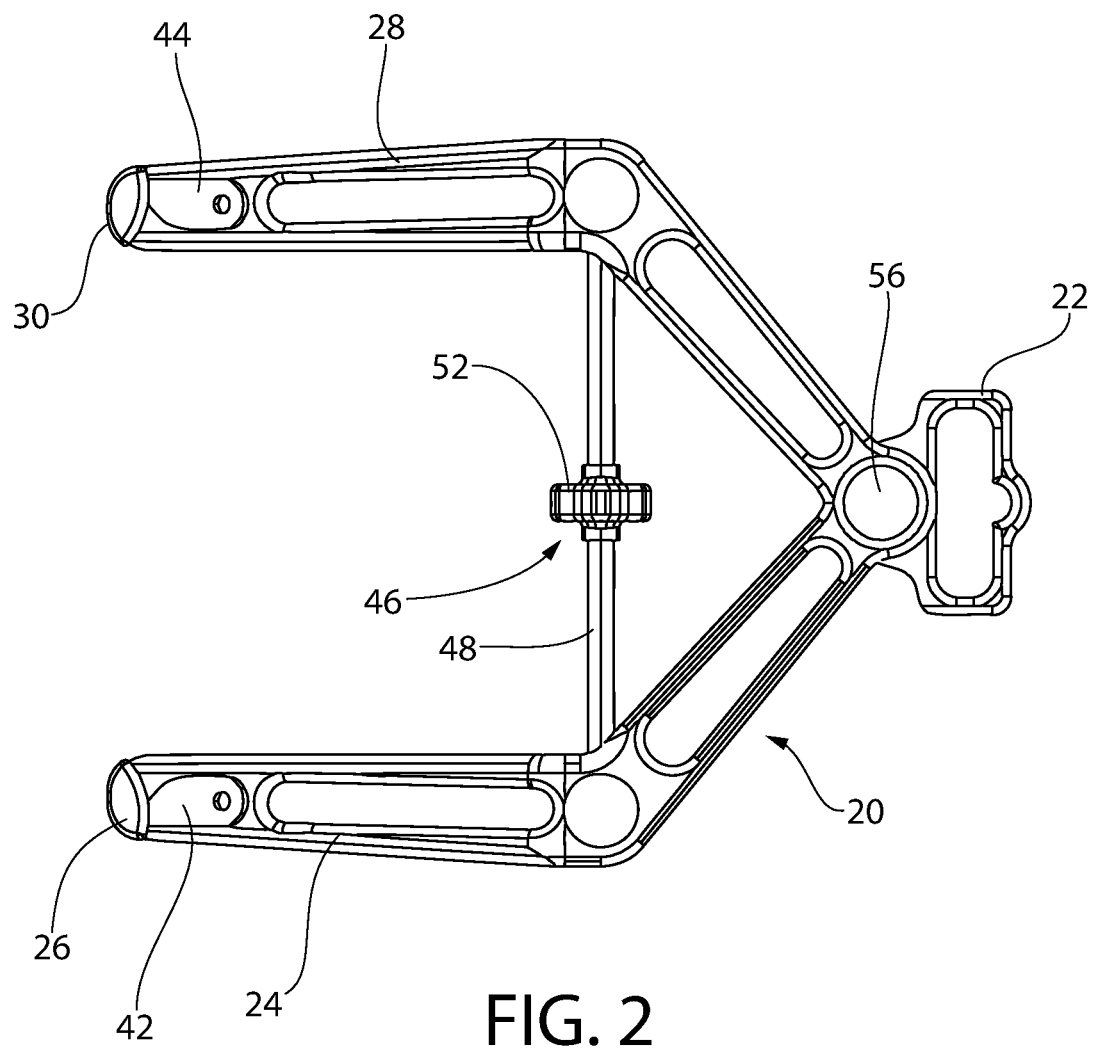
FIG. 2 is a top plan view of an orthopedic fixation assembly according to an embodiment of the present disclosure.
Figure 3:
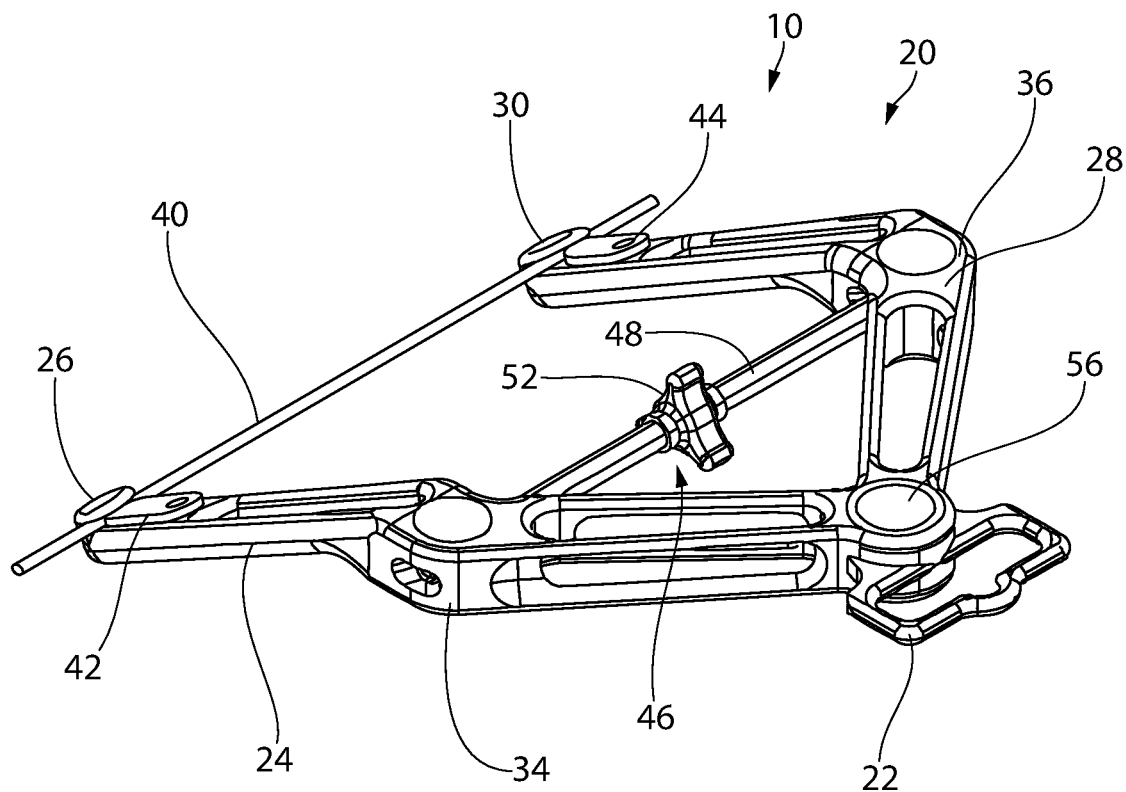
FIG. 3 is a perspective view of an orthopedic fixation assembly according to an embodiment of the present disclosure.
Figure 4:
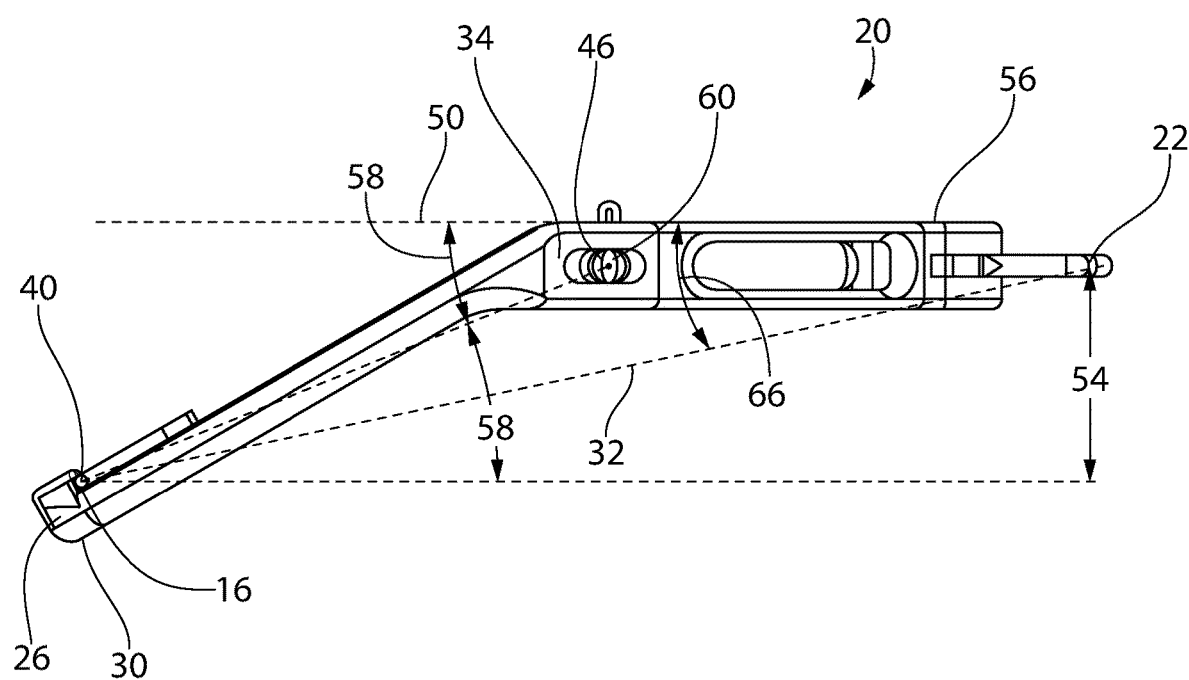
FIG. 4 is a right side elevation view of an orthopedic fixation assembly according to an embodiment of the present disclosure.

Referring now to FIGS. 2-4, the fixation assembly 20 further includes a first arm 24 having a first arm end portion 26 and a second arm 28 having a second arm end portion 30. The fixation assembly 20 further includes a joint 56 connecting the first arm 24 to the second arm 28 for adjustment of the first arm 24 and/or the second arm 28, or the adjustment of either the first arm 24 or the second arm 28 relative to the other, along an adjustment plane 50.

As illustrated in FIG. 4, the first arm end portion 26, the second arm end portion 30, and the attachment portion 22 define an end plane 32. The first arm 24 includes a first arm central portion 34, and the second arm 28 includes a second arm central portion 36. As illustrated in FIG. 4, the first arm central portion 34 and the second arm central portion 36 are spaced from the end plane 32. The first arm end portion 26 is distal from the joint 56 and angled from the adjustment plane 50 by a downward angle 58, and the second arm end portion 30 being distal from the joint 56 and angled from the adjustment plane 50 by the downward angle 58. In the embodiment illustrated in FIG. 4, the downward angle 58 is measured from a rotational axis 60 of an adjustment member 46, discussed in further detail below, to the traction location 16 or elongate member 40, discussed in further detail below, relative to the adjustment plane 50. The downward angle 58 of the illustrated embodiment is approximately 30 degrees, but is between 10 and 60 degrees in an embodiment and between 15 and 45 degrees in another embodiment.

Referring again to FIG. 3 with continuing reference to FIG. 1, the system 10 and/or the fixation assembly 20 includes an elongate member 40 secured at the first arm end portion 26 and the second arm end portion 30. The system 10 may include the fixation assembly 20 and the elongate member 40 in one embodiment. In the embodiment illustrated in FIG. 3, the elongate member 40 is a Kirschner-type pin. In additional embodiments not illustrated, the elongate member 40 is a wire or any other structure configured to function similarly to a pin or wire. As shown in FIG. 2-4, the fixation assembly 20 includes a first securing member 42 at the first arm end portion 26 and a second securing member 44 at the second arm end portion 30. The first securing member 42 and the second securing member 44 are configured to cooperatively secure the elongate member 40 at the traction location 16, as described in further detail below and illustrated in further detail in FIGS. 5 and 6.

The fixation assembly 20 includes the adjustment member 46 disposed between the first arm 24 and the second arm 28 and configured to adjust a position of the first arm 24 relative to the second arm 28. The adjustment member 46 adjusts the first arm 24 and the second arm 28 along the adjustment plane 50 angled from the end plane 32, as illustrated in FIG. 4. The end plane 32 is angled from the adjustment plane 50 by an end plane angle 66 falling in the range of between 5 degrees and 60 degrees in one embodiment, falling in the range of between 10 degrees and 45 degrees in another embodiment, and of approximately 15 degrees in another embodiment. Referring still to FIG. 4, the traction location 16 and/or position of the elongate member 40 may be offset from the adjustment plane 50 by an offset distance 54. The offset distance 54 is between 1 and 5 inches in one embodiment, between 2 inches and 4 inches in another embodiment, and approximately 2.5 inches in another embodiment.

The adjustment member 46 is disposed at the first arm central portion 34 and the second arm central portion 36, as best illustrated in FIGS. 3 and 4. In an embodiment, the adjustment member 46 includes a threaded rod 48 rotatable to adjust the position of the first arm 24 relative to the second arm 28. The adjustment member 46 includes a turnbuckle structure or function in one or more embodiments. The adjustment member 46 of the embodiment illustrated in FIG. 3 includes an adjustment knob 52. The adjustment knob 52 is rigidly coupled to the threaded rod 48 such that rotation by a user of the adjustment knob 52 results in adjustment of the position of the first arm 24 relative to the second arm 28. With the elongate member 40 secured at the first arm end portion 26 and the second arm end portion 30, the operation of the adjustment member 46, such as by rotation of the adjustment knob 52, results in an increase or decrease of tension on the elongate member 40.

Figure 5:
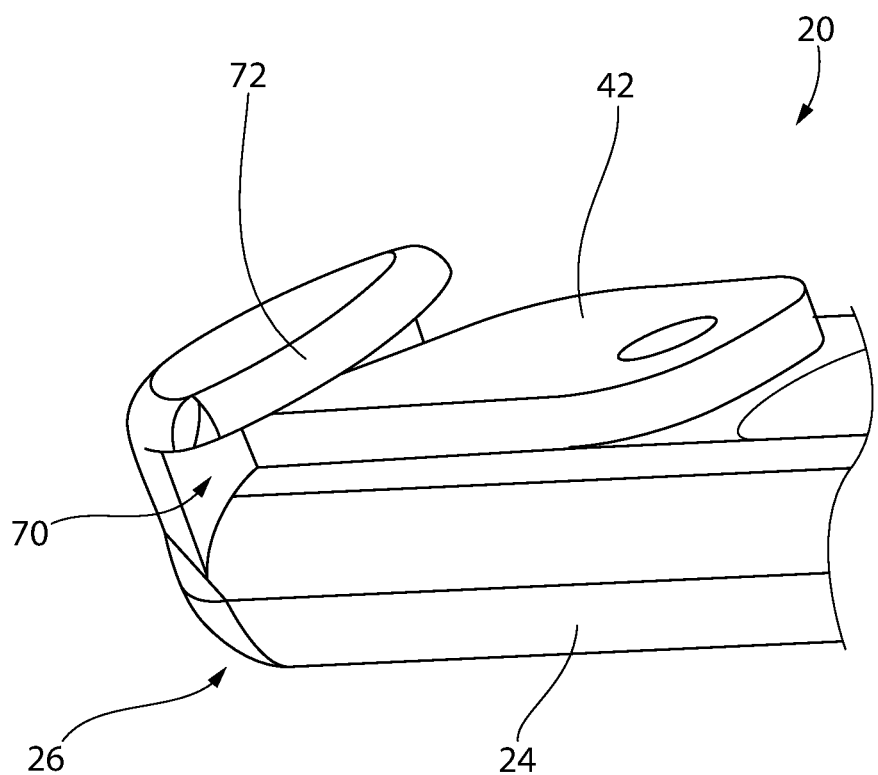
FIG. 5 is an enlarged perspective view of an orthopedic fixation assembly according to an embodiment of the present disclosure.
Figure 6:
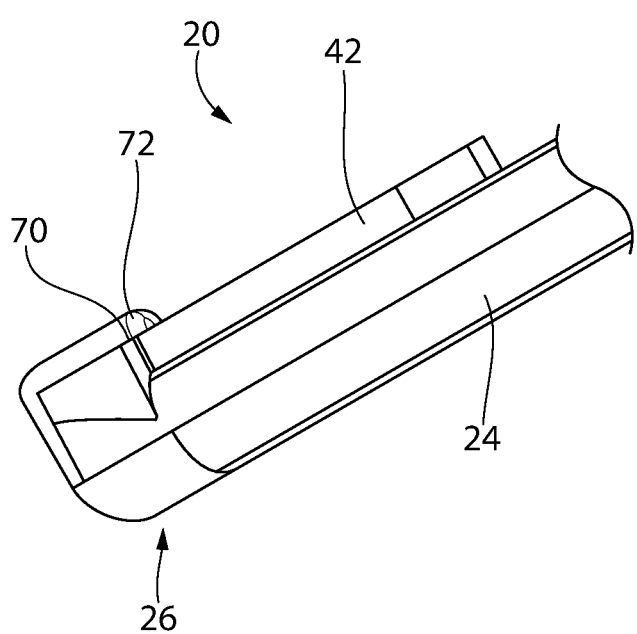
FIG. 6 is an enlarged side elevation view of an orthopedic fixation assembly according to an embodiment of the present disclosure.

FIGS. 5 and 6 are enlarged views of the first arm end portion 26 having the first securing member 42 of the fixation assembly 20. Although not illustrated in the enlarged views of FIGS. 5 and 6, the features of the first arm end portion 26 are mirrored to form the second arm end portion 30 having the second securing member 44 of the fixation assembly 20. Therefore, any structure or function described with regard to the first arm end portion 26 forms part of the second arm end portion 30. As described above and illustrated in FIGS. 3 and 4, the first securing member 42 and the second securing member 44 are configured to cooperatively secure the elongate member 40 at the traction location 16. As best illustrated in FIG. 6, the first arm end portion 26 includes a channel 70 formed by a lip 72. The lip 72 extends in a direction parallel to or at least substantially parallel to the first securing member 42, as illustrated in FIGS. 5 and 6. The channel 70 extends in a direction perpendicular to or at least substantially perpendicular to the direction of extension of the lip 72, as illustrated in FIGS. 5 and 6. As illustrated in the embodiments of FIGS. 3 and 6, the first securing member 42, upon securing the elongate member 40 to the first arm end portion 26 via pivotal attachment of the first securing member 42 to the first arm 24, is positioned at least partially in the channel 70 and/or at least partially between the first arm 24 and the lip 72. As illustrated in FIGS. 3 and 4, the elongate member 40 is then secured at the end of the first securing member 42 within the channel 70.

The system 10 and assembly 20 of various embodiments described and illustrated herein provide an orthopedic fixation or traction bow system or assembly providing a desired tractive force without discomfort or injury to the patient. The configuration of the first arm 24, the second arm 28, and the adjustment member 46 results in the first arm central portion 34 and the second arm central portion 36 being spaced from the end plane 32. Such spacing provides a clearance from the limb 62 or other body part undergoing traction. As illustrated in FIG. 1, the clearance prevents or reduces pressure, impacts, sores, and other maladies resulting from contact with the limb 62 at a contact location 64 with conventional devices.

The system 10 and assembly 20 of various embodiments described and illustrated herein may be at least partially made from any metal or ceramic material. In one or more embodiments, the system 10 and the assembly 20 may be at least partially made from a plastic, elastomeric, and/or composite material. One or more composite materials include, without limitation, fiber reinforced plastics, synthetic materials, and/or any other material known by those having ordinary skill in the art. Such plastic, elastomeric, and/or composite material construction enables the assembly 20 to enter and/or be near and/or exposed to specialized medical machinery, including without limitation particular imaging machines. Further, such plastic, elastomeric, and/or composite material construction enables the assembly 20 to remain coupled with the elongate member 40 and/or in place with the patient for a longer period of time without multiple or frequent removal and/or installation. In an embodiment, the assembly 20 is made completely from a plastic, elastomeric, and/or composite material. It will be further appreciated that, while particular pin(s), rod(s), fastener(s), the elongate member 40, and/or other hardware portion(s) of the assembly 20 may be made from metal or ceramic in particular embodiments, the assembly 20 being at least partially made from plastic, elastomeric, and/or composite material construction reduces the weight of the assembly 20, thereby enhancing the handling of the assembly 20, improves comfort of the patient due to the assembly 20 having a lower weight, and/or reduces the manufacturing and shipping costs of the system 10 and/or the assembly 20.

Further, the system 10 and the assembly 20 of various embodiments described and illustrated herein offer improved handling and control due to the adjustment member 46, including the easily accessed and rotated adjustment knob 52. The minimal number of interconnected parts connecting the adjustment member 46 to the arms 24, 28 results in improved control. A user may precisely adjust tension on the elongate member 40 with precise operation of the adjustment knob 52 due to the minimal number of moving parts. Additionally, the system 10 and the assembly 20 improve user control by allowing adjustment by rotating the adjustment knob 52 about the axis 60. Adjustment by rotation in a direction about an axis perpendicular to the elongate member 40 would undesirably increase tension on and/or bending of the elongate member 40 and/or create potential discomfort for the patient. The adjustment knob 52 is rotated about the axis 60 of the system 10 and the assembly 20, which is parallel to the elongate member 40, rather than rotating an adjustment member in a direction about an axis perpendicular to the elongate member 40, thereby improving control and patient comfort.

While the disclosure has been illustrated and described in detail in the drawings and foregoing description, the same is to be considered as illustrative and not restrictive in character, it being understood that only certain embodiments have been shown and described and that all changes and modifications that come within the spirit of the disclosure are desired to be protected.

What is claimed is:

1. An orthopedic fixation assembly comprising:
   a first arm configured for positioning at a first side of a traction location;
   a second arm configured for positioning at a second side of the traction location; and
   a joint connecting the first arm to the second arm for adjustment of the first arm and the second arm along an adjustment plane, the first arm having a first arm end portion being distal from the joint and angled from the adjustment plane by a deflection angle, and the second arm having a second arm end portion being distal from the joint and angled from the adjustment plane by the deflection angle;
   wherein an attachment portion is configured for attachment to a stationary traction member, wherein the attachment portion, the first arm end portion, and the second arm end portion form an end plane angled from the adjustment plane;
   wherein the end plane is angled from the adjustment plane by between 15 degrees and 60 degrees; and
   wherein once said attachment portion is attached to said stationary traction member, a resulting traction force is applied along a traction vector outside of said end plane.

2. The assembly of claim 1, further including a first securing member at the first arm end portion and a second securing member at the second arm end portion, wherein the first securing member and the second securing member are configured to cooperatively secure an elongate member at the traction location.

3. The assembly of claim 1, further comprising an adjustment member disposed between the first arm and the second arm and configured to adjust a relative position of the first arm relative to the second arm.

4. The assembly of claim 3, wherein the adjustment member is disposed along the adjustment plane.

5. The assembly of claim 3, wherein the adjustment member includes a threaded rod rotatable to adjust the relative position of the first arm relative to the second arm.

6. The assembly of claim 1, wherein the first arm and the second arm are made from at least one of a plastic, elastomeric, and composite material.

7. An orthopedic fixation system comprising:
   a stationary traction member configured to apply a pulling force to a traction location; and
   a traction bow assembly configured for positioning at the traction location and having an attachment portion attached to the stationary traction member, a first arm having a first arm end portion, and a second arm having a second arm end portion, an end plane defined between the first arm end portion, the second arm end portion, and the attachment portion, the first arm having a first arm central portion and the second arm having a second arm central portion such that the first arm central portion and the second arm central portion are spaced from the end plane;
   wherein the traction bow assembly further includes an adjustment member disposed between the first arm and the second arm and configured to adjust a relative position of the first arm relative to the second arm;
   wherein the adjustment member adjusts the first arm and the second arm along an adjustment plane angled from the end plane;

wherein the end plane is angled from the adjustment plane by between 15 degrees and 60 degrees; and wherein once said attachment portion is attached to said stationary traction member, the said pulling force is applied along a traction vector outside of said end plane.

8. The system of claim 7, further comprising an elongate member secured at the first arm end portion and the second arm end portion.

9. The system of claim 7, wherein the adjustment member is disposed at the first arm central portion and the second arm central portion.

10. The system of claim 7, wherein the adjustment member includes a threaded rod rotatable to adjust the position of the first arm relative to the second arm.

11. A traction bow assembly comprising:
an attachment portion configured for attachment to a stationary traction member;
a first arm comprising:
  a first arm end portion distal from the attachment portion; and
  a first arm central portion;
a second arm comprising:
  a second arm end portion distal from the attachment portion; and
  a second arm central portion;
wherein the first arm end portion, the second arm end portion, and the attachment portion form an end plane, and the first arm central portion and second arm central portion are spaced from the end plane;
wherein an adjustment member disposed between the first arm and the second arm and configured to adjust a position of the first arm relative to the second arm,
wherein the adjustment member is disposed along an adjustment plane angled from the end plane by between 15 degrees and 60 degrees; and
wherein once said attachment portion is attached to said stationary traction member, a resulting traction force is applied along a traction vector outside of said end plane.

12. The assembly of claim 11, further comprising:
a first securing member at the first arm end portion; and
a second securing member at the second arm end portion, wherein the first securing member and the second securing member are configured to cooperatively secure an elongate member.

13. The assembly of claim 11, wherein the adjustment member includes a threaded rod rotatable to adjust the relative position of the first arm relative to the second arm.

* * * * *